United States Patent
Satoh et al.

(10) Patent No.: US 7,229,414 B2
(45) Date of Patent: Jun. 12, 2007

(54) PULSE WAVE MEASURING APPARATUS THAT CAN OBTAIN OPTIMUM PRESSURIZATION FORCE OF PRESSURE SENSOR

(75) Inventors: Hironori Satoh, Moriyama (JP); Tomoki Kitawaki, Okayama (JP); Yoshinori Miyawaki, Otsu (JP)

(73) Assignee: Omron Healthcare Co., Ltd., Kyoto (JP)

( * ) Notice: Subject to any disclaimer, the term of this patent is extended or adjusted under 35 U.S.C. 154(b) by 445 days.

(21) Appl. No.: 10/822,736

(22) Filed: Apr. 13, 2004

(65) Prior Publication Data

US 2004/0210142 A1 Oct. 21, 2004

(30) Foreign Application Priority Data

Apr. 15, 2003 (JP) ............................. 2003-110734

(51) Int. Cl.
*A61B 5/00* (2006.01)
(52) U.S. Cl. ....................................... 600/485; 600/501
(58) Field of Classification Search ......... 600/485–504
See application file for complete search history.

(56) References Cited

U.S. PATENT DOCUMENTS

| | | | |
|---|---|---|---|
| 5,094,244 A * | 3/1992 | Callahan et al. | 600/490 |
| 5,119,822 A | 6/1992 | Niwa | |
| 5,279,303 A * | 1/1994 | Kawamura et al. | 600/496 |
| 5,494,043 A | 2/1996 | O'Sullivan et al. | |
| 5,497,779 A * | 3/1996 | Takaya et al. | 600/485 |
| 5,836,887 A | 11/1998 | Oka et al. | |
| 5,873,834 A * | 2/1999 | Yanagi et al. | 600/485 |
| 5,997,540 A * | 12/1999 | Zheng et al. | 606/64 |
| 6,022,320 A * | 2/2000 | Ogura et al. | 600/490 |
| 6,527,726 B2 * | 3/2003 | Goto et al. | 600/485 |
| 2002/0065471 A1 * | 5/2002 | Amano et al. | 600/485 |
| 2002/0161305 A1 | 10/2002 | Oka | |
| 2004/0171941 A1 * | 9/2004 | Narimatsu et al. | 600/485 |
| 2004/0193061 A1 * | 9/2004 | Sato et al. | 600/500 |

FOREIGN PATENT DOCUMENTS

| | | |
|---|---|---|
| EP | 1 440 655 | 7/2004 |
| JP | 01-232929 A | 9/1989 |
| JP | 02-109540 A | 4/1990 |
| JP | 279682 | 9/1998 |
| JP | 2798682 | 9/1998 |
| JP | 2000-166887 A | 6/2000 |
| JP | 2004-222847 A | 8/2004 |

OTHER PUBLICATIONS

European Search Report dated Aug. 31, 2004 relating to EP Application No. 04007706.7.

* cited by examiner

*Primary Examiner*—Max Hindenburg
*Assistant Examiner*—Karen E Toth
(74) *Attorney, Agent, or Firm*—Morrison & Foerster LLP

(57) ABSTRACT

A pulse wave measuring apparatus extracts a direct current component from a pressure value obtained from a sensor pressure, and defines the pressurization force of the cuff as the optimum pressurization force when that direct current component is stable. Following determination of the optimum pressurization force, the pulse wave measuring apparatus monitors whether the direct current component obtained from the pressure sensor is optimum or not, and adjusts the pressure, when not. By determining the rising sharpness of the peak and waveform distortion in the sphygmographic waveform, determination is made whether the pressurization force of the cuff is appropriate or not to carry out further adjustment of pressure, as necessary.

10 Claims, 8 Drawing Sheets

FIG.8
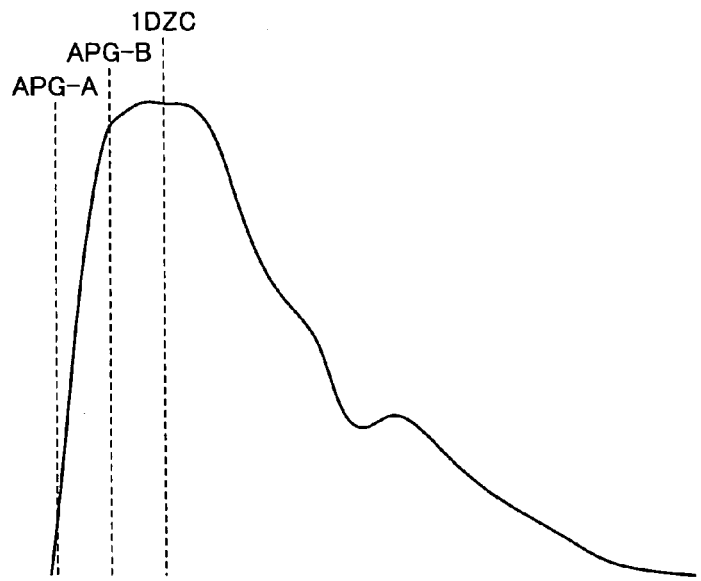
FIG.9
| NUMBER OF 4DZC POINTS | | TYPE CLASSIFICATION | POSSIBILITY OF EXCESSIVE PRESSURIZATION |
|---|---|---|---|
| APG-A POINT ~ APG-B POINT | APG-B POINT ~ 1DZC POINT | | |
| 3 OR MORE POINTS | | ERROR | HIGH |
| 1 | 0~1 | $\gamma, \delta$ | MODERATE |
| 0 | 1 | $\gamma, \delta$ | LOW |
| 0 | 0 | $\alpha, \beta$ | NONE |
FIG.10
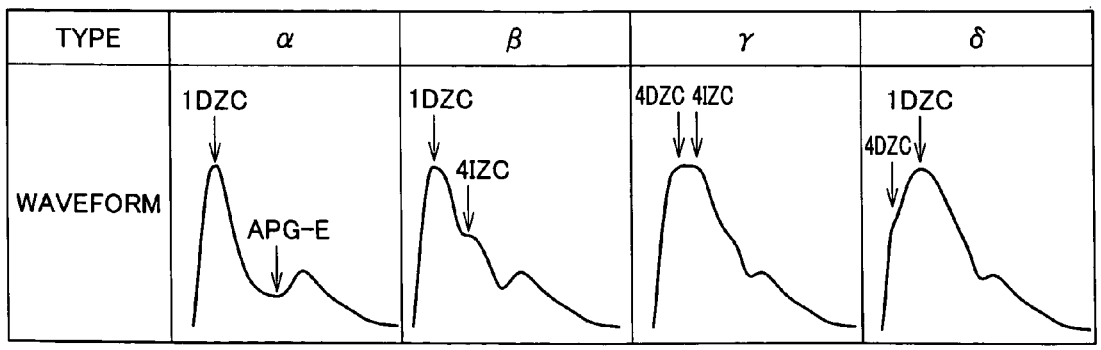

PULSE WAVE MEASURING APPARATUS THAT CAN OBTAIN OPTIMUM PRESSURIZATION FORCE OF PRESSURE SENSOR

BACKGROUND OF THE INVENTION

1. Field of the Invention

The present invention relates to a pulse wave measuring apparatus and a pulse wave measuring apparatus control program product. Particularly, the present invention relates to a pulse wave measuring apparatus and a pulse wave measuring apparatus control program product that can obtain optimum pressurization force of a pressure sensor.

2. Description of the Background Art

In pulse wave measuring apparatuses detecting pulse waves, the pressurization force to press the pressure sensor against a measurement site of a subject is an important parameter.

One such method of obtaining an optimum pressurization force is disclosed in, for example, Japanese Patent No. 2798682.

In such a conventional sphygmograph apparatus, the function of separating a pulse wave of each beat from the voltage signal obtained from the pressure sensor is required to obtain the optimum pressurization force. There is a problem that the operation processing has become more complicated to render difficult reduction in size of the apparatus.

Furthermore, the sphygmograph apparatus disclosed in the aforementioned Japanese Patent No. 2798682 has the problem that waveform distortion and the like at the maximum blood pressure region is not taken into account since attention is focused on the change at the lowest blood pressure region of the pulse wave when the pressurization force is altered.

SUMMARY OF THE INVENTION

In view of the foregoing, an object of the present invention is to provide a pulse wave measuring apparatus and a pulse wave measuring apparatus control program product that can obtain the optimum pressurization force of a pressure sensor with simple operation processing.

According to an aspect of the present invention, a pulse wave measuring apparatus includes a pressure sensor detecting an intra-arterial pressure waveform superficial of a body, an acquiring unit of acquiring a direct current component from a pressure value output from the pressure sensor, and a defining unit of defining the pressurization force of the pressure sensor against a body surface as the optimum pressurization force when the direct current component is stable.

According to another aspect of the present invention, a pulse wave measuring apparatus includes a pressure sensor detecting an intra-arterial pressure waveform superficial of a body, and a determination unit determining whether the pressurization force of the pressure sensor against a body surface is appropriate or not based on a sphygmographic waveform detected by the pressure sensor.

According to still another aspect of the present invention, a pulse wave measuring apparatus control program product is a program to cause a computer to execute control of a pulse wave measuring apparatus including a pressure sensor detecting an intra-arterial pressure waveform superficial of the body. The program product causes the computer to execute the steps of acquiring a direct current component from a pressure value output from the pressure sensor obtained from the pulse wave measuring apparatus, and defining the pressurization force of pressing the pressurization sensor against the body surface as the optimum pressurization force when the direct current component is stable.

According to still another aspect of the present invention, a pulse wave measuring apparatus control program product is a program causing a computer to control a pulse wave measuring apparatus including a pressure sensor detecting an intra-arterial pressure waveform superficial of the body. The program products causes the computer to execute the steps of acquiring a sphygmographic waveform detected by the pressure sensor from the pulse wave measuring apparatus, and determining whether the pressurization force of the pressure sensor against the body surface is appropriate or not based on the acquired sphygmographic waveform.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 8 is a diagram to describe classification of the waveform types.

FIG. 9 shows a specific example of a classification table of waveform types.

FIG. 10 schematically shows waveforms of types $\alpha$-$\delta$.

DESCRIPTION OF THE PREFERRED EMBODIMENTS

Figure 1:
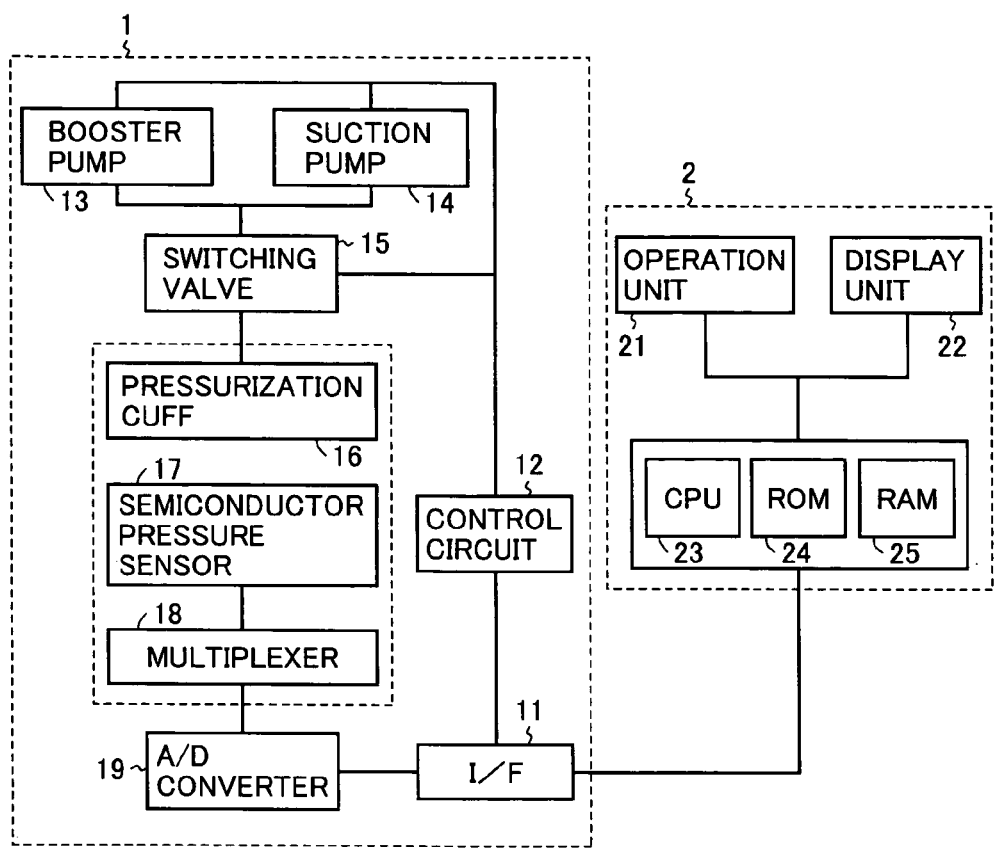
FIG. 1 shows a specific structure of a pulse wave measuring apparatus in accordance with an embodiment.

Embodiments of the present invention will be described hereinafter with reference to the drawings. In the following description, the same components and elements have the same reference character allotted. Their designation and function are identical. Therefore, detailed description thereof will not be repeated.

Referring to FIG. 1, a pulse wave measuring apparatus according to the present embodiment is mainly formed of a pulse wave device 1 detecting a pulse wave, and a control device 2 providing control of the entire pulse wave measuring apparatus. Pulse wave device 1 and control device 2 are connected through a dedicated cable such as a USB (Universal Serial Bus) cable, a communication line, or the like. It is assumed that connection thereof also includes non-contact connection such as radio communication.

Control device 2 includes a ROM (Read Only Memory) 24 and a RAM (Random Access Memory) 25 storing data and programs to control the pulse wave measuring apparatus, and a CPU (Central Processing Unit) 23 providing control of the entire pulse wave measuring apparatus. CPU 23 establishes access to ROM 24 to read out a program, which is transferred to RAM 25 for execution, whereby overall control of the pulse wave measuring apparatus is effected. Control device 2 also includes an operation unit 21 operated to input various information provided in a manner operable from an external source, and a display unit 22 formed of a LED (Light Emitting Diode), a LCD (Liquid Crystal Display), or the like to output various information such as the artery position detection and pulse wave measurement result. CPU 23 receives an operation signal through operation unit 21 designated by a user to carry out control processing of the pulse wave measuring apparatus based on the operation signal. Specifically, CPU 23 responds to the operation signal input through operation unit 21 to send out a control signal to pulse wave device 1. CPU 23 also displays the measurement result and the like received from pulse wave device 1 at display unit 22.

Control device 2 is generally a computer or the like. The structure of control device 2 shown in FIG. 1 is a specific example of a general computer structure. Therefore, the structure of control device 2 is not limited to that shown in FIG. 1.

Pulse wave device 1 receives the control signal from control device 2 via an I/F 11. The control signal received at I/F 11 is transmitted to a control circuit 12, and then to a booster pump 13, a suction pump 14, or a switching valve 15.

Booster pump 13 functions to increase the inner pressure (referred to as cuff pressure hereinafter) of a pressurization cuff (air bag) 16. Suction pump 14 functions to reduce the cuff pressure. Switching valve 15 selectively connects one of booster pump 13 and suction pump 14 to an air pipe (not shown). Control circuit 12 provides control thereof.

A semiconductor pressure sensor 17 includes a plurality of sensor elements aligned at a predetermined interval in one direction on a semiconductor chip formed of single crystalline silicon or the like. Semiconductor pressure sensor 17 is pressed against a measurement site such as the wrist of a subject during measurement by the pressure of pressurization cuff 16. Under this state, semiconductor pressure sensor 17 detects the pulse wave of a subject via an arteria radialis. Semiconductor pressure sensor 17 applies voltage signals output by detecting a pulse wave to a multiplexer 18 for each channel of respective sensor elements.

Multiplexer 18 selectively provides the voltage signal output from respective sensor elements to an A/D converter 19. A/D converter 19 converts the voltage signal that is an analog signal provided from semiconductor pressure sensor 17 into digital information. The digital information is transmitted to control device 2 via I/F 11. In the present embodiment, CPU 23 obtains at the same time voltage signals output from respective sensor elements in semiconductor pressure sensor 17 along the time axis via multiplexer 18.

In FIG. 1, the present pulse wave measuring apparatus is implemented with pulse wave device 1 and control device 2 to conduct pulse wave measurement in cooperation. Alternatively, the pulse wave measuring apparatus may include pulse wave device 1 and control device 2 in an integral manner.

The process carried at the pulse wave measuring apparatus of the present embodiment will be described with reference to the flow chart of FIG. 2. The process of the flow chart of FIG. 2 is realized by CPU 23 of control device 2 establishing access to ROM 24 to read out a program therefrom, which is transferred onto RAM 25 for execution.

Figure 2:
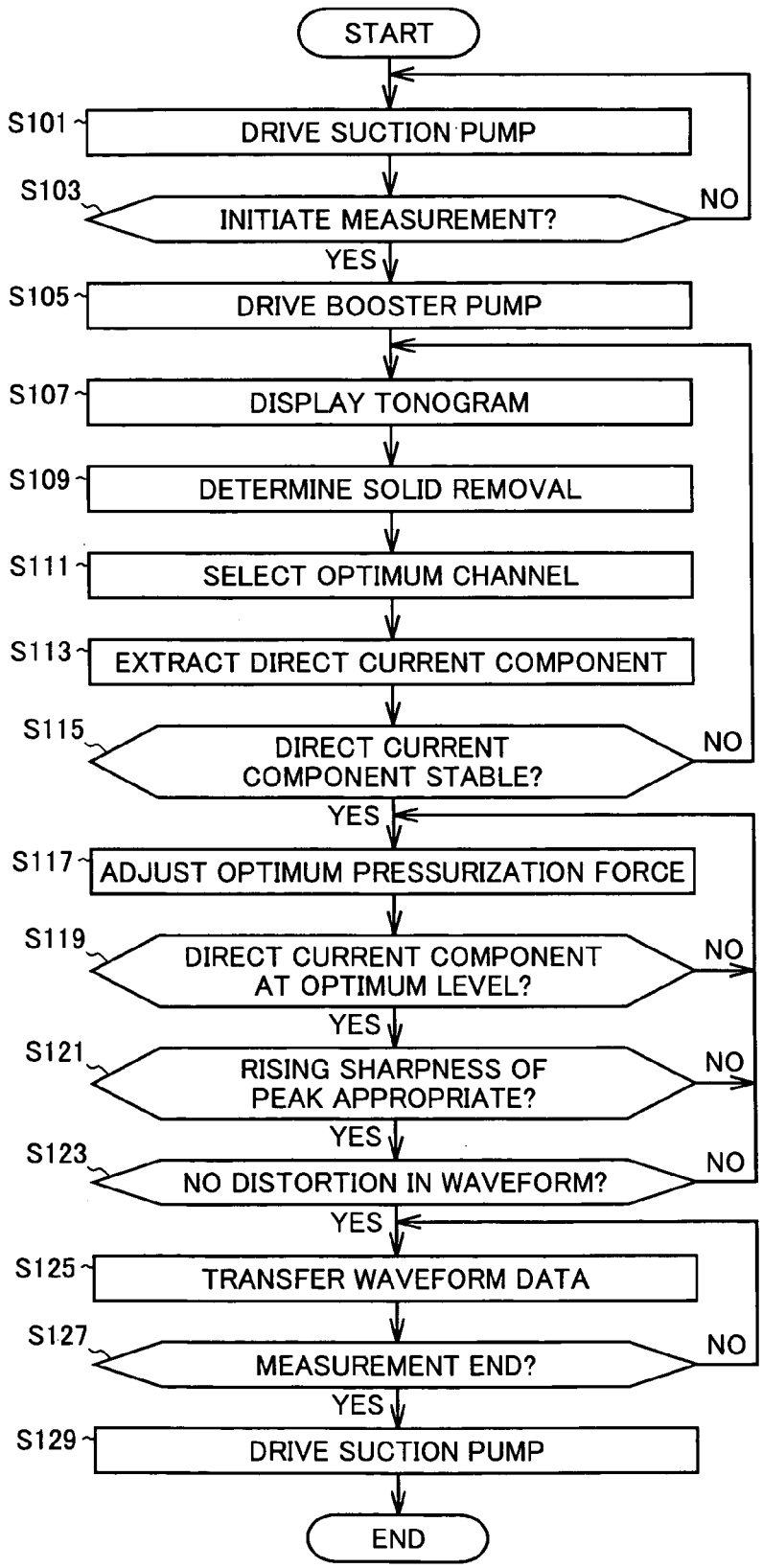
FIG. 2 is a flow chart of the process carried out at the pulse wave measuring apparatus of the embodiment.

Referring to FIG. 2, in response to a power switch (not shown) turned on, CPU 23 instructs control device 12 to drive suction pump 14 via I/F 11. In response to this instruction, control circuit 12 switches valve 15 towards suction pump 14 to drive suction pump 14 (S101). Suction pump 14 is driven so that the cuff pressure is set sufficiently lower than the atmosphere through switching valve 15. This avoids unnecessary protrusion of the sensor unit including semiconductor pressure sensor 17 that will cause erroneous operation or failure.

Then, initiation of measurement is identified by detecting movement of the sensor portion to the measurement site, or depression of a measurement start switch (not shown) in operation unit 21 (S103). In the case of the former, the sensor portion includes a microswitch or the like not shown to sense movement. CPU 23 determines whether the sensor portion has moved or not based on the detection signal of that microswitch.

When determination is made that measurement has initiated (YES at S103), CPU 23 sends a control signal to control device 12 via I/F 11 so as to drive booster pump 13. Control circuit 12 responds to this control signal to switch valve 15 towards booster pump 13 to drive booster pump 13 (S105). Accordingly, the cuff pressure rises, whereby the sensor unit including semiconductor pressure sensor 17 is pressed against the surface of the measurement site of the subject.

Upon pressurization of the sensor portion against the measurement site, voltage signals from respective sensor elements in semiconductor pressure sensor 17 are provided via multiplexer 18. The voltage signals are converted into digital information at A/D converter 19, and then applied to CPU 23 via I/F 11. CPU 23 generates a tonogram based on the received digital information. The generated tonogram is displayed at display unit 22 (S107).

CPU 23 determines the presence of solids such as the tendon, radius, or the like subcutaneous of the measurement site, based on the tonogram generated at step S107, to execute a process removing the solid (S109). In this solid removal process, the sensor element with a sensing region in which the region above the solid is included is identified from the sensor elements in semiconductor pressure sensor 17, based on the information from the tonogram obtained at S107. The other sensor elements excluding the identified sensor element are selected as the candidates of sensor elements whose detection region corresponds to a region above an artery. The solid removal process is not limited to that described in the present invention. For example, the approach disclosed in Japanese Patent Application No. 2003-12313 previously filed by the applicant of the present invention can be used.

CPU 23 executes the process to select, from the candidates of sensor elements, the sensor elements whose detection region corresponds to a region above an artery as the optimum channels (S111). The process of selecting the optimum channels is not limited to that described in the present invention. The approach disclosed in the aforementioned Japanese Patent Application No. 2003-12313 can be employed.

CPU 23 extracts the direct current component from the voltage signals applied from respective sensor elements corresponding to the selected optimum channels (S113). The direct current component is obtained from the average value of voltage signals over a constant time, the component of the voltage signal passing through a low pass filter (component removed of pulse wave), or the level of the voltage signal at the pulse wave rising point (immediately before mixture of pulse wave component).

Figure 3:
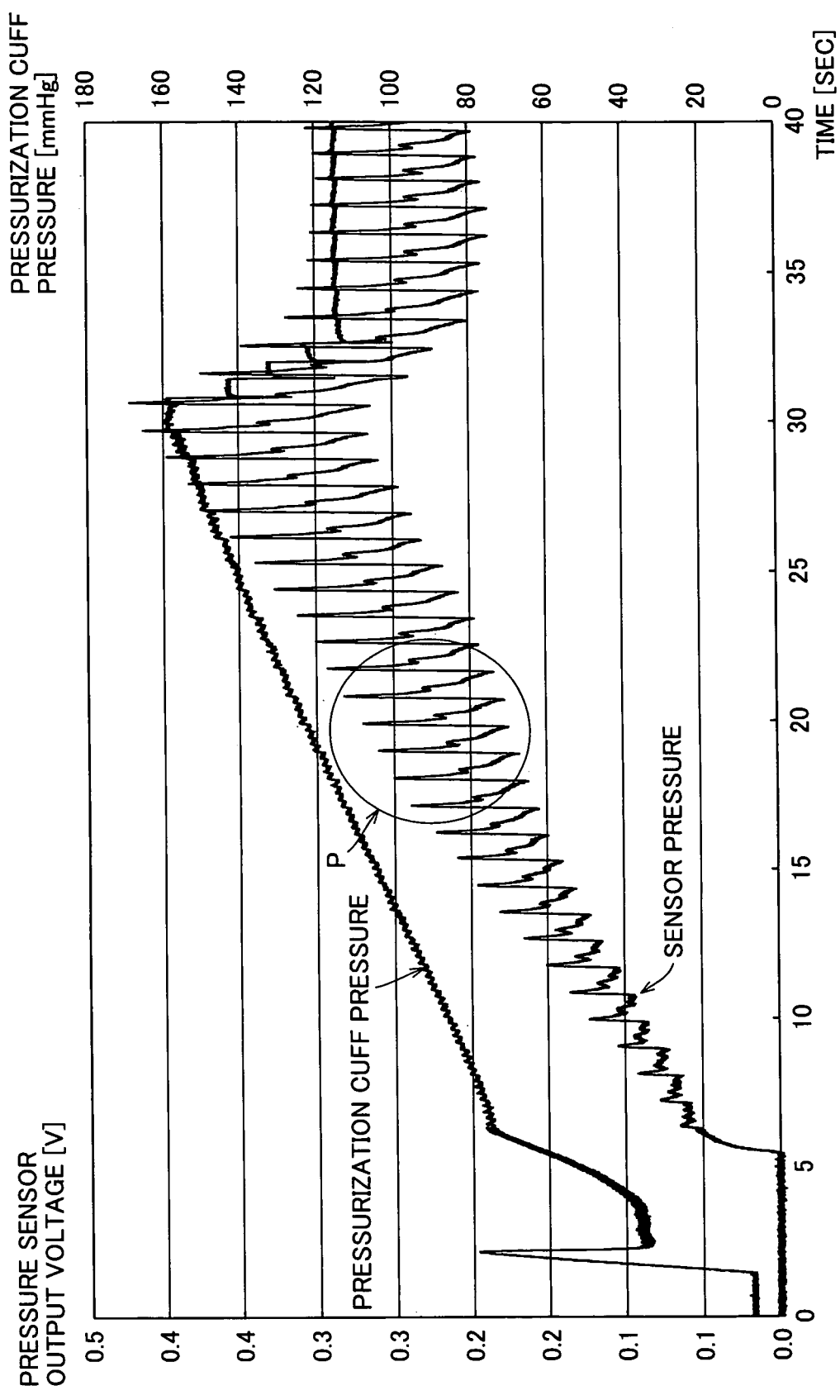
FIG. 3 shows a specific example of change in the output of a semiconductor pressure sensor 17 during pulse wave measurement.

Specifically, change in the output of semiconductor pressure sensor 17 during pulse wave measurement will be described based on the graph of FIG. 3. In the graph of FIG. 3, the level of the voltage signal output from semiconductor pressure sensor 17 and the pressurization level by pressurization cuff 16 on the sensor portion are plotted along the ordinate, whereas the elapse of the pulse wave measurement time is plotted along the abscissa.

Figure 4:
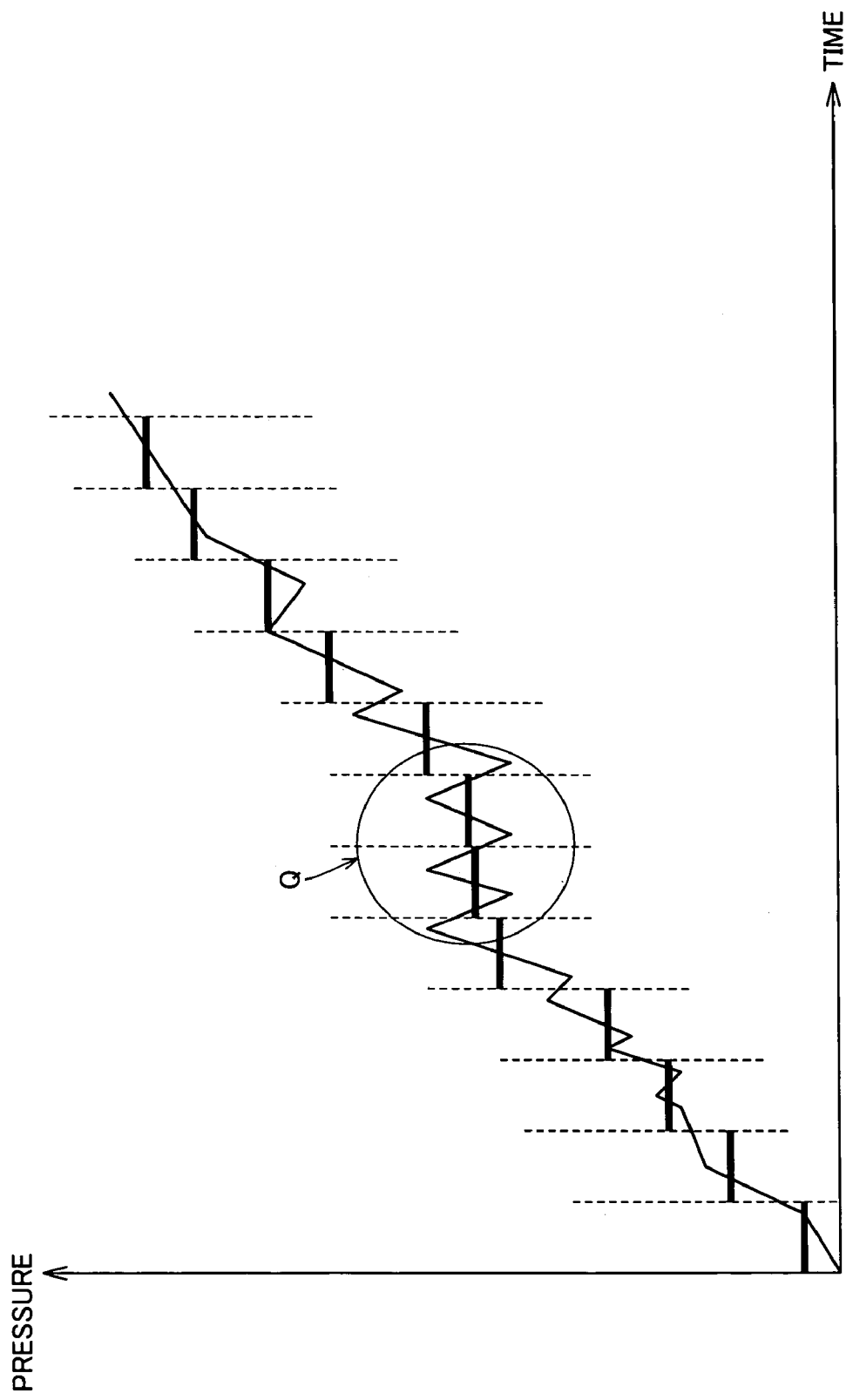
FIG. 4 shows a specific example of a direct current component.

The pulse wave measuring apparatus of the present invention is characterized in that the direct current component is extracted by dividing the output change of the voltage signal shown in FIG. 3 into windows (interval) for each predetermined time, and calculating the average of each window. FIG. 4 shows a specific example of the direct current component extracted from the change in the output voltage signal of FIG. 3. Alternatively, the direct current component can be extracted by calculating the intermediate value between the highest value and lowest value in each window, or extracting the value below a predetermined frequency using a low pass filter, or the like. The aforementioned predetermined time is the time interval preset at the pulse wave measuring apparatus independent of the pulse beat of the subject. Preferably, the time interval is set to approximately 1.5 seconds in which the time of one pulse beat is included.

Since the pulse wave measuring apparatus of the present invention does not use the sphygmographic waveform of every one beat, and extracts the direct current component from the division of windows for each predetermined time, the pulse wave measuring apparatus can obtain a direct current component through a simple operation, dispensable of the conventional process of separating a pulse wave from the obtained voltage signal for each beat. Accordingly, the complexity of the pulse wave measuring apparatus can be reduced. Furthermore, the processing speed required for extracting a direct current component can be increased.

CPU 23 then detects the site where the direct current component extracted at step S113 from the voltage signals applied through respective sensor elements corresponding to the selected optimum channels is stable (S115). Specifically, CPU 23 detects the encircled region Q of the direct current component shown in FIG. 4 as the site where the direct current component is stable at step S115. The encircled region Q of FIG. 4 corresponds to the encircled region P of FIG. 3. In other words, the encircled portion P in FIG. 3 representing the change in the output of the voltage signal from semiconductor pressure sensor 17 is detected as the site where the direct current component is stable since change in the output relative to change in the cuff pressure of pressurization cuff 16 is small.

Upon detection of a site where the direct current component is stable (YES at S115), CPU 23 defines the pressurization force of pressurization cuff 16 at that time point as the optimum pressurization force, and sends a control signal to control circuit 12 via I/F 11 so as to adjust the pressure of pressurization cuff 16 (S117).

In the case where a site where the direct current component is stable is not detected (NO at S115), the process of the above-described steps S107–S115 is repeated while continuing pressurization of pressurization cuff 16 through booster pump 13 until a site where the direct current component is stable is detected.

The pulse wave measuring apparatus of the present invention is further characterized in that the determination process of steps S119–S123 set forth below is carried out repeatedly even after a pressurization force of pressurization cuff 16 is defined as the optimum pressurization force at step S117. This is directed to conduct fine adjustment for the purpose of maintaining the optimum pressurization force. Specifically, CPU 23 continuously monitors whether the direct current component is stable or not under the state where the pressurization force of pressurization cuff 16 is adjusted at the level of the optimum pressurization (S119). For the purpose of maintaining the pressurization force of pressurization cuff 16 at the optimum pressurization level, adjustment of the pressurization force of step S117 is repeated, as necessary (NO at S119).

More specifically, at step S117, CPU 23 switches valve 15 to booster pump 13, and alters the pressurization force of semiconductor pressure sensor 17 by increasing the pressurization force of pressurization cuff 16 at a constant rate or an arbitrary rate through booster pump 13, or switches valve 15 to suction pump 14, and alters the pressurization force of semiconductor pressure sensor 17 by reducing the pressurization force of pressurization cuff 16 at a constant rate or arbitrary rate through suction pump 14 to adjust the pressurization force. The direct current component corresponding to the definition of the optimum pressurization force at step S119 is compared with the direct current component succeeding adjustment of the pressurization force so as to adjust, if necessary, the pressurization force, avoiding excessive pressurization.

Then, CPU 23 determines whether the rising sharpness of the peak of the voltage signal output from the sensor element selected as the optimum channel under the state where pressurization force of pressurization cuff 16 is maintained at the optimum pressurization level, i.e. the waveform data, is appropriate or not (S121), and further determines whether there is waveform distortion or not (S123). The process of detection at step S121 and step S123 will be described afterwards.

When the rising sharpness of the peak of the waveform data is not appropriate (NO at S121), or when waveform distortion is detected (NO at S123), adjustment of the pressurization force of step S117 is repeated until the rising sharpness of the peak of waveform data becomes appropriate, or until waveform distortion is no longer detected.

When the rising sharpness of the peak of waveform data is appropriate (YES at S121), and when waveform distortion is not detected (YES at S123), CPU 23 acquires waveform data of that time point from pulse wave device 1 via multiplexer 18, A/D converter 19 and I/F 11 (S125).

CPU 23 detects a pulse wave from the waveform data acquired from pulse wave device 1 to determine establishment of a predetermined condition of waveform detection end (S127). The condition to end waveform detection of step S127 may be an elapse of a preset predetermined time, or an end (or interruption) instruction from a user. In other words, the above-described transfer process of pulse wave data of step S125 is repeated until a predetermined condition is established. The pulse wave detection process based on acquired waveform data can be conducted by well known procedures. Therefore, details thereof will not be provided here.

When the predetermined condition to end pulse wave detection is established (YES at S127), CPU 23 sends a control signal to control device 12 via I/F 11 so as to drive suction pump 14 via switching valve 15 (S129). Thus, the pressurized status of the sensor portion relative to the measurement site is released, and the series of pulse wave detection process ends.

Figure 5:
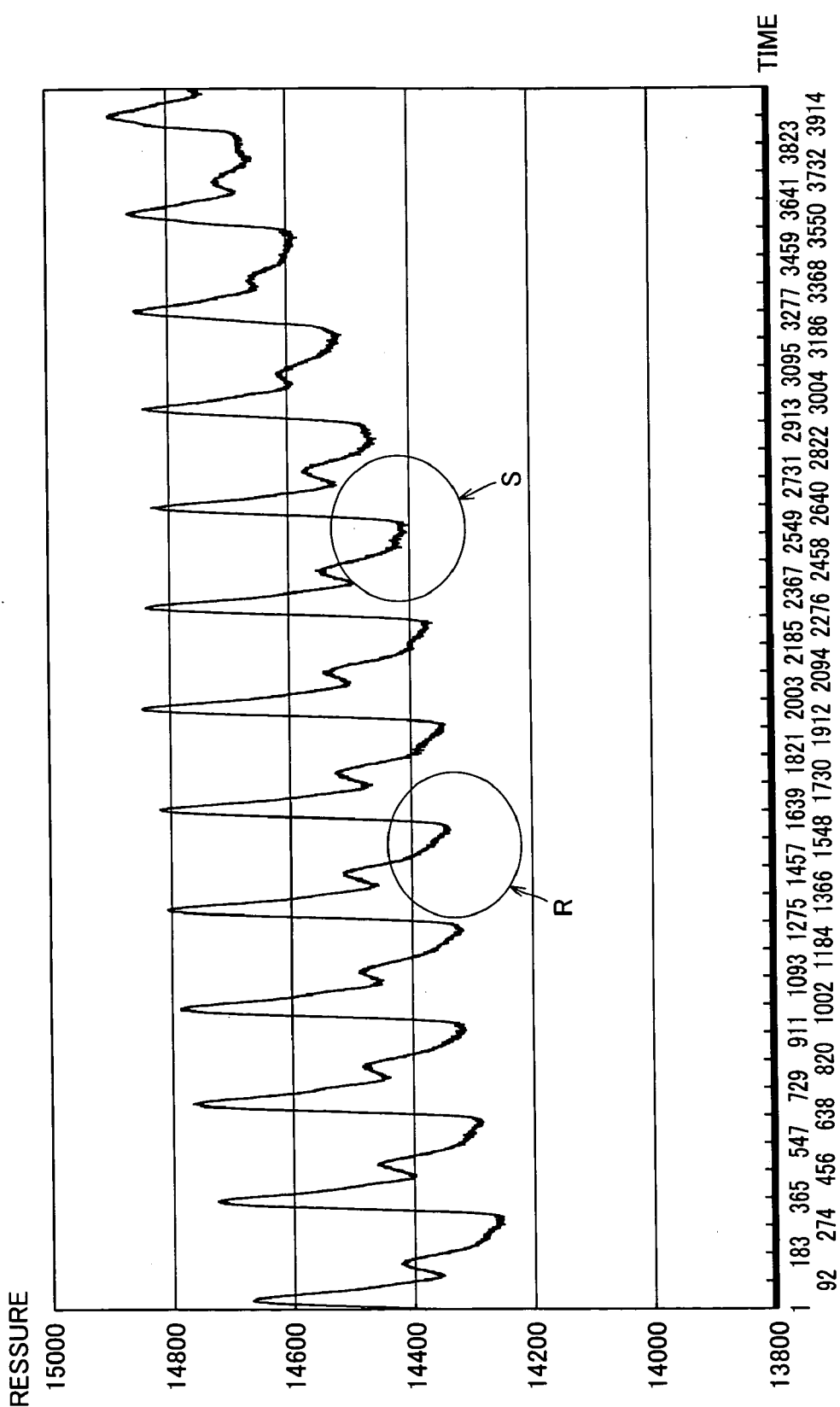
FIG. 5 shows a specific example of change in the output of semiconductor pressure sensor 17 during pulse wave measurement.
Figure 6:
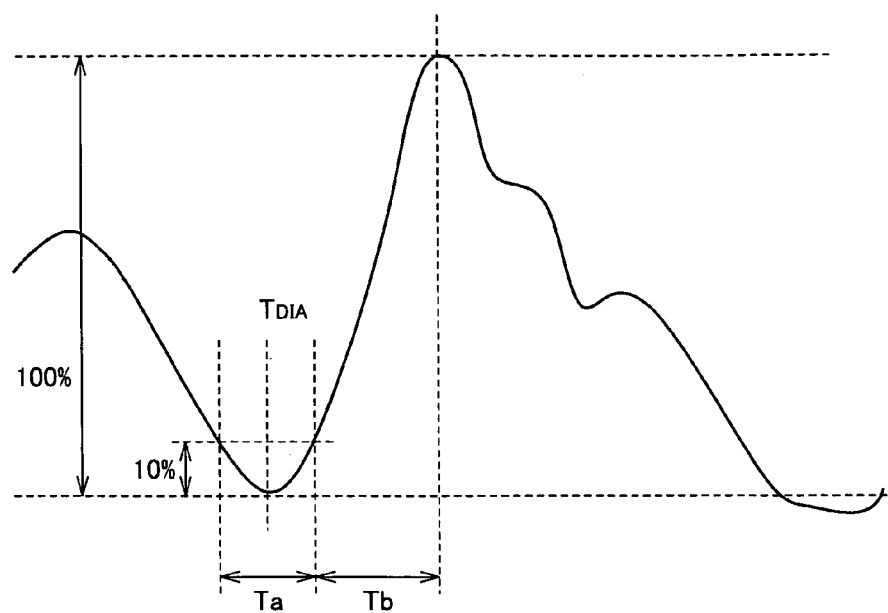
FIG. 6 is a diagram to describe the calculation method of a rising sharpness of the peak (MSP).

Determining the rising sharpness of the peak (MSP) at step S121 will be described in detail with reference to FIGS. 5 and 6.

The rising sharpness of the peak of the output change from semiconductor pressure sensor 17 is an index explicitly representing the pressurization force of pressurization cuff 16. In the encircled portion R of FIG. 5, the rising point of the change in the output of semiconductor pressure sensor 17 is sharp, implying that the pressurization force of pressurization cuff 16 of that interval is appropriate. On the other hand, in the encircled portion S of FIG. 5, the rising point of the change in the output of semiconductor pressure sensor 17 is rather flattened, i.e. blunt, implying that the pressurization force of pressurization cuff 16 of that interval is not appropriate. This means that the artery subcutaneous of the measurement site is pressed harder than needed. The pulse wave measuring apparatus of the present embodiment is characterized in that determination is made whether the pulse wave is measured under an appropriate pressurization force of pressurization cuff 16 or not by determining whether the calculated value of the rising sharpness of the peak of waveform data is appropriate or not.

The method of calculating and determining the rising sharpness of the peak (MSP) at step S121 will be described with reference to FIG. 6. FIG. 6 shows a specific example of change in the output of semiconductor pressure sensor 17 for one pulse beat with the level of the voltage signal output from semiconductor pressure sensor 17 plotted along the ordinate and the pulse wave measurement time plotted along the abscissa.

First, a predetermined breakpoint ($T_{DIA}$) is set. Two points higher by 10% than the amplitude at that breakpoint of the maximum amplitude are extracted. Then, MSP=Ta/Tb is calculated, where Ta is the time interval between the extracted two points, and Tb is the time from the end point of the two points to the pulse wave peak.

Then, with variable n=0, the current amplitude value AMP (n), the current pressurization force P (n) of pressurization cuff 16, and the current rising sharpness of the peak MSP (n) are sequentially stored. When the rising sharpness of the peak MSP (n) is below a preset value (for example 2.0) (MSP (n)<preset value), determination is made that the rising sharpness of the peak (MSP) is appropriate (YES at S121). Calculation of the rising sharpness of the peak is terminated, and control proceeds to the process of step S123.

In the case where the rising sharpness of the peak MSP (n) is lower than the initial value of MSP (0) (MSP (0)> MSP (n)), the current pressurization force P (n) is set as the optimum pressure of pressurization cuff 16. Adjustment is made so as to attain that optimum pressure at step S117. When MSP (n−1)/MSP (n) is lower than a preset value (for example 2.0) for two times in a row (MSP (n−1)/ MSP (n)<preset value), determination is made that the rising sharpness of the peak (MSP) is appropriate (YES at S121). Calculation of the rising sharpness of the peak ends, and control proceeds to the next step S123. Alternatively, in the case where the current amplitude value AMP (n) is below 50% the initial value of AMP (0) (AMP (0)×50%>AMP (n)), calculation of the rising sharpness of peak ends, and control proceeds to the next step S123.

When these conditions are not satisfied, the optimum pressurization force of pressurization cuff 16 is reduced by a predetermined value (for example 10 mmHg), and the above-described process is repeated. Further, when the rising sharpness of the peak (MSP) becomes equal to or higher than a preset value (for example 2.0) (MSP (n)>preset value), the optimum pressurization force of pressurization cuff 16 is reduced by a predetermined value, and the above-described process is repeated.

Determination of the aforementioned waveform distortion at step S123 will be described in detail with reference to FIGS. 7–9.

Figure 7:
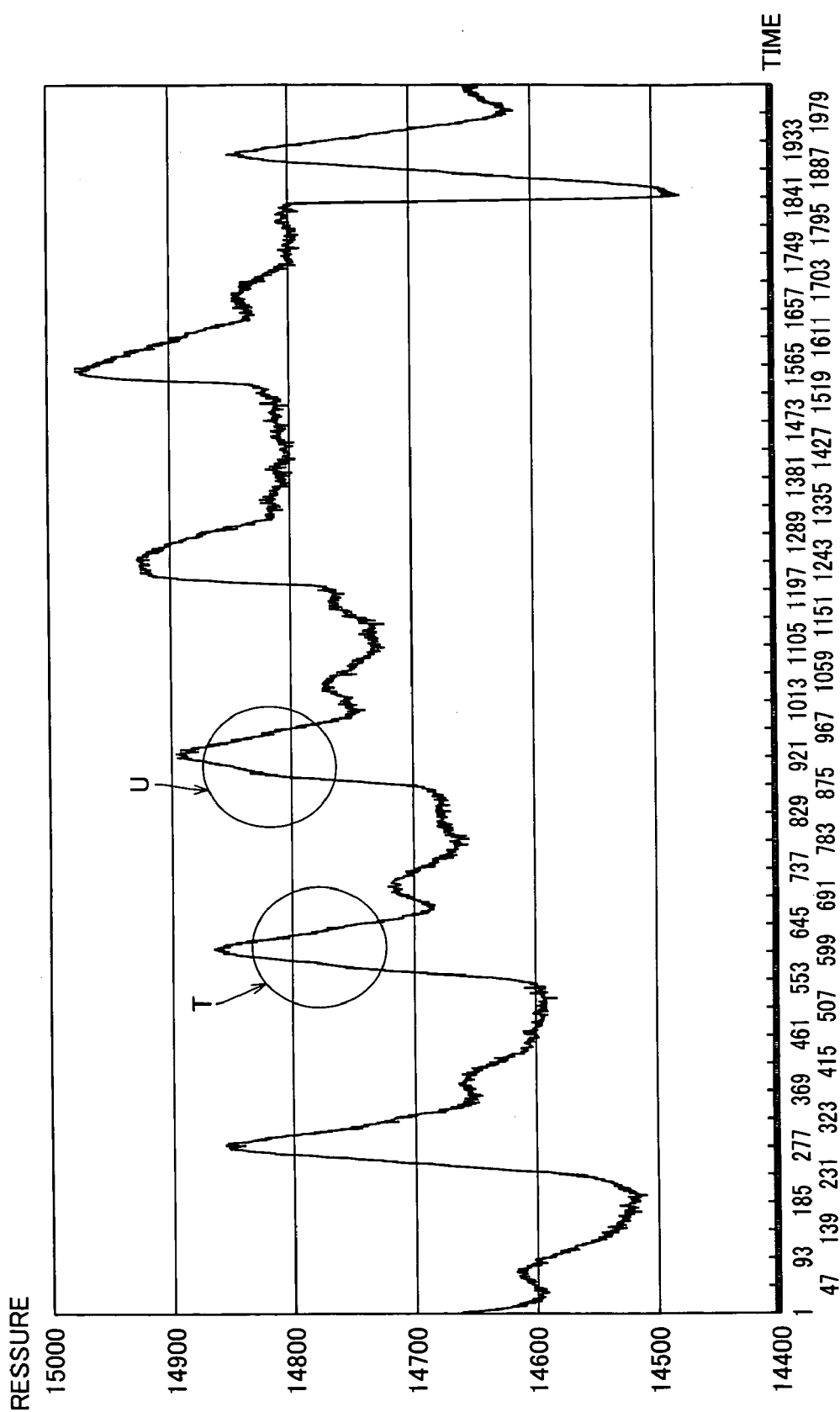
FIG. 7 shows a specific example of change in the output of semiconductor pressure sensor 17 during pulse wave measurement.

When the pressurization force of pressurization cuff 16 is not appropriate, distortion occurs in the output waveform of semiconductor pressure sensor 17, as shown in FIG. 7. Taking advantage of this generation of waveform distortion, the pulse wave measuring apparatus of the present embodiment is characterized in that determination is made whether the waveform is measured at the appropriate pressurization force of pressurization cuff 16 by determining the presence of distortion in the output waveform of semiconductor pressure sensor 17 at step S123. The determination method of waveform distortion at step S123 will be described here with reference to FIGS. 8 and 9.

Notation of respective characteristic points in a waveform is defined as follows:

1DZC: positive-to-negative zero crossing point of first derivative

4DZC: positive-to-negative zero crossing point of fourth derivative

4IZC: negative-to-positive zero crossing point of fourth derivative

APG-A: acceleration pulse wave point A
APG-B: acceleration pulse wave point B
APG-E: acceleration pulse wave point E
APG-F: acceleration pulse wave point F The above 1DZC (positive-to-negative zero crossing point) is a point on a waveform corresponding to point zero at the transition from + to − of first derivative, and represents the maximal point such as the pulse wave highest point. 4DZC is a point on a waveform corresponding to point zero at the transition from + to − of fourth derivative, whereas 4IZC (negative-to-positive zero crossing point) is a point on a waveform corresponding to point zero at the transition from − to + of fourth derivative, both representing an inflection point or distortion in a waveform. APG-A to APG-F are points on a waveform corresponding to respective points A-F, where A-F are respective peaks of second derivative, representing the characteristics of respective waveforms.

At step S123, the aforementioned characteristic points are calculated based on the output waveforms from semiconductor pressure sensor 17, and classified into their waveform types. Waveform types are classified in accordance with the classification table shown in FIG. 9, focusing on the number and respective positions of 4DZCs located between APG-A point to 1DZC point. Referring to FIG. 9, when there are three or more 4DZC points in the region of APG-A point to APG-B point and APG-B point to 1DZC point, determination is made of an error based on type classification since there are too many waveform distortions. Determination is made that the possibility of the pressurization force of pressurization cuff 16 being excessive is high (NO at S123). In this case, control returns to step S117. Adjustment is made so as to reduce the pressurization force of pressurization cuff 16, and the process of steps S119–S123 is repeated.

When there is one 4DZC point in the region of APG-A point to APG-B point, and zero to one 4DZC points in the region of APG-B point to 1DZC point, determination is made that the waveform type is γ or δ. Determination is made that the possibility of the pressurization force of pressurization cuff 16 being excessive is moderate (NO at S123). In this case, control returns to step S117. Adjustment is made so as to reduce the pressurization force of pressurization cuff 16, and the process of steps S119–S123 is repeated.

In addition, when there is no 4DZC point in the region of APG-A point to APG-B point, and there is one 4DZC point in the region of APG-B point to 1DZC point, determination is made that the waveform type is y or 6. Determination is made that the possibility of the pressurization force of pressurization cuff 16 being excessive is low (YES at S123). Further, when there is no 4DZC point in the region of APG-A point to APG-B point and APG-B point to 1DZC point, determination is made that the waveform type is α or β. Determination is made that there is no possibility of the pressurization force of pressurization cuff 16 being excessive (YES at S123). Then, control proceeds to step S125.

The schematic forms of waveform types α-δ set forth above are as shown in FIG. 10. Since the details of each waveform type is not essential to the present invention, description thereof will not be provided here.

When there is the 4DZC point between APG-A point and 1DZC point, the augmentation index (referred to as AI hereinafter) often exceeds 1.0 (also represented as 100%). Therefore, determination can be made that the possibility of the pressurization force of pressurization cuff 16 being excessive is moderate when AI exceeds 1.0.

Therefore, determination of the possibility of the pressurization force being excessive by identifying the number of 4DZC points can be substituted with the calculation of AI.

The pulse wave measuring apparatus of the present invention repeatedly carries out the determination of steps S119–S123 even after a pressurization force of pressurization cuff 16 is defined as the optimum pressurization force to allow fine adjustment, thus maintaining the pressurization force at the optimum level. Therefore, the pressurization force of pressurization cuff 16 can be maintained at the optimum pressurization level, absent of any distortion in the pulse waveform. Even if waveform distortion occurs, the pressurization force of pressurization cuff 16 can be modified to a pressurization force that eliminates generation of waveform distortion, whereby the pressurization force of pressurization cuff 16 is maintained at the optimum level. In other words, the pulse wave measuring apparatus of the present invention can define the optimum pressurization force by simple calculation, and then obtain measurement results while maintaining the optimum pressurization force. Thus, the pulse wave measuring apparatus of the present invention can obtain measurement results of favorable precision with high speed processing without increasing the complexity of the apparatus.

The direct current component extraction method, the rising sharpness of the peak (MSP) calculation and determination method, and the waveform determination method of the pulse wave measuring apparatus can be provided in the form of a program. Such a program can be stored in a computer-readable recording medium such as a flexible disc, CD-ROM (Compact Disc-ROM), ROM, RAM or memory card associated with a computer to be provided as a program product. Alternatively, the program can be recorded in a recording medium such as a hard disk incorporated in a computer to be provided as a program. Furthermore, the program can be provided by downloading through a network.

The presented program product is installed in a program storage unit such as a hard disk for execution. The program product includes the program itself, and the recording medium in which the program is recorded.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A pulse wave measuring apparatus comprising:
   a pressure sensor detecting an intra-arterial pressure waveform superficial of a body,
   an acquiring unit acquiring a direct current component from a pressure value output from said pressure sensor, and
   a defining unit including means for detecting a site where said direct current component is stable, for defining a pressurization force of pressing said pressure sensor against a body surface as an optimum pressurization force, when said direct current component is stable.

2. The pulse wave measuring apparatus according to claim 1, wherein said acquiring unit acquires said direct current component from an average value between predetermined intervals of pressure values output from said pressure sensor.

3. The pulse wave measuring apparatus according to claim 1, wherein said acquiring unit acquires said direct current component from an intermediate point between a highest value and a smallest value in a predetermined interval of pressure values output from said pressure sensor.

4. The pulse wave measuring apparatus according to claim 1, wherein said acquiring unit acquires said direct current component using a low pass filter on pressure values output from said pressure sensor.

5. The pulse wave measuring apparatus according to claim 1, further comprising a booster unit altering said pressurization force by applying pressure at one of a constant rate and an arbitrary rate.

6. The pulse wave measuring apparatus according to claim 5, further comprising a first adjustment unit comparing said direct current component at a time when said optimum pressurization force is defined with a direct current component after altering said pressurization force, and carrying out adjustment such that the direct current component after altering said pressurization force does not exceed said direct current component at the time when said optimum pressurization force was defined.

7. The pulse wave measuring apparatus according to claim 1, further comprising a suction unit altering said pressurization force by reducing pressure at one of a constant rate and an arbitrary rate.

8. The pulse wave measuring apparatus according to claim 7, further comprising a first adjustment unit comparing said direct current component at a time when said optimum pressurization force is defined with a direct current component after altering said pressurization force, and carrying out adjustment such that the direct current component after altering said pressurization force does not exceed said direct current component at the time when said optimum pressurization force was defined.

9. The pulse wave measuring apparatus according to claim 1, further comprising:
   a determination unit determining whether the pressurization force of said pressure sensor against said body surface is appropriate or not based on a sphygmographic waveform detected by said pressure sensor, and
   an adjustment unit adjusting said pressurization force after defining said optimum pressurization force based on said determination result.

10. A computer-readable medium containing instructions for causing a computer to execute control of a pulse wave measuring apparatus including a pressure sensor detecting an intra-arterial pressure waveform superficial of a body, by a method comprising:

acquiring a direct current component from a pressure value output from said pressure sensor obtained from said pulse wave measuring apparatus, and detecting a site where said direct current component is stable, for defining a pressurization force of pressing said pressure sensor against a body surface as an optimum pressurization force, when said direct current component is stable.

* * * * *